United States Patent [19]

Konno

[11] Patent Number: 4,667,513

[45] Date of Patent: May 26, 1987

[54] METHOD AND APPARATUS FOR DETECTING MUSCLE FATIGUE

[76] Inventor: Yohio Konno, 12-18, Jinnan, 1-Chome, Shibuya-Ku, Tokyo 150, Japan

[21] Appl. No.: 838,880

[22] PCT Filed: Mar. 18, 1981

[86] PCT No.: PCT/JP81/00059
§ 371 Date: Nov. 17, 1982
§ 102(e) Date: Nov. 17, 1982

[87] PCT Pub. No.: WO82/03166
PCT Pub. Date: Sep. 30, 1982

Related U.S. Application Data

[63] Continuation of Ser. No. 448,992, Nov. 17, 1982, abandoned.

[51] Int. Cl.⁴ .............................................. A61B 5/22
[52] U.S. Cl. ................................... 73/379; 128/774; 128/733
[58] Field of Search .................. 73/379; 128/733, 774; 364/415

[56] References Cited

U.S. PATENT DOCUMENTS

| 3,442,132 | 5/1969 | DeMare | 73/379 |
| 3,670,573 | 6/1972 | Kroemer | 73/379 |
| 3,905,355 | 9/1975 | Brudny | 128/733 |
| 4,213,467 | 7/1980 | Stulen et al. | 128/733 |

OTHER PUBLICATIONS

Gandy et al.—"Acquisition and Analysis of Electromyographic Data . . . Arm", Medical and Bilogical Engineering and Computing, Jan. 1980, pp. 57–64.

Primary Examiner—Charles A. Ruehl
Attorney, Agent, or Firm—Guy W. Shoup

[57] ABSTRACT

A method of and an apparatus for estimating the degrees of the fatigue and pain of muscles and comparing subjects of different weights on the same basis by deriving the variation in the muscular strength such as the dorsal muscular strength, shoulder muscular strength, the grasping power, and the like as an electric signal and integrating the muscular output on one hand, providing an integrated value of the electromyogrammatic amplitude by processing the voltage induced from the muscle to be tested through an electromyogram amplitude and a waveform processor, and by digitally displaying the ratio between these integrated values after correcting the ratio with a weight/muscular strength coefficient.

31 Claims, 9 Drawing Figures

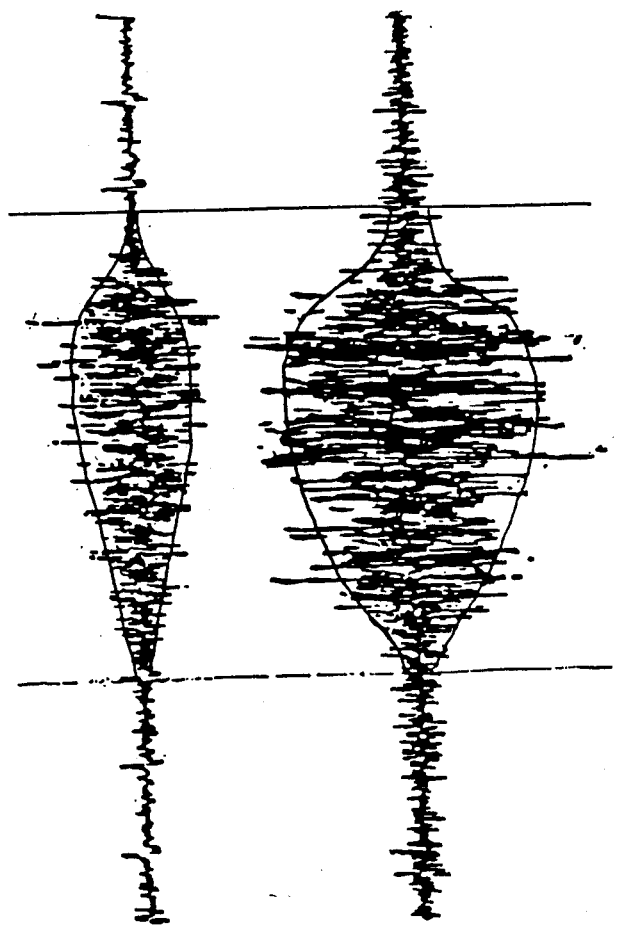

METHOD AND APPARATUS FOR DETECTING MUSCLE FATIGUE

This is a continuation application from application Ser. No. 448,992 filed Nov. 17, 1982, now abandoned; based on International Application No: PCT/JP81/00059, filed Mar. 18, 1981.

TECHNICAL FIELD

The present invention relates to a method of and an apparatus for detecting muscle fatigue or pain. In particular, the present invention relates to a method of digitally representing the ratio between the integral or integrated value of the electromyogrammatic amplitude of the muscle being tested to the integrated value of the muscular output representing the variation in muscular strength corrected by the weight/muscular strength coefficient. The present invention relates also to an apparatus for displaying the muscular strength, the maximum discharge amount (mV) of the muscle being tested and the ratio between the integrals of the electromyogrammatic amplitude and the muscular strength on a panel display by passing the muscular strength such as dorsal muscular strength, shoulder arm strength and grasping power through a transducer for providing an electric signal, an amplifier for amplifying the electric signal, an electromyogram amplifier coupled with detection electrodes for deriving an action potential from the part of muscle being tested, and a waveform processor for processing the waveform.

BACKGROUND ART

In a conventional load electromyogram used for measurement of fatigue by an electromygram, the load often has a constant value. For example, an experiment on arm bending utilizing an ergometer was an experiment on the fatigue resulting from repeated movements of raising a weighted body to a definite position, and not an experiment about the muscular strength and the electromyogram in the process of reaching the maximum muscular strength. It was also impossible to know whether or not the subject is already tired or feels pain at the time of measurement and, if he is tired or feels pain, what its degree is.

The inventor reported a method of recording the discharge amount derived from a muscle being tested and the muscular strength of the muscle being tested as a muscular strength electromyogram on a recorder by passing the discharge amount through an input means and further an electromyogram amplifier on the one hand, and by passing the muscular strength through a transducer to convert it into an electric signal which is supplied to an amplifier on the other hand, the muscular strength and electromyogrammatic signals from these amplifiers being supplied to a recorder amplifier and then to the recorder ("Industrial Medicine," Vol. 18, No. 4, 1976, pp. 383 to 390). It has been found from the muscular strength electromyogram obtained by this method that the amplitude of the electromyogram increases as the muscular strength increases and the discharge amount of the muscle at the time of fatigue is higher than that when not tired. It has also been found that when the muscle is dead tired, the discharge amount increases considerably in spite of reduced muscular strength. However, there is a problem to this method that the degrees of fatigue cannot be exactly compared numerically.

Also the inventor has found it necessary to find the areas of muscular strength electromyograms to obtain the ratio therebetween in order to exactly compare the degrees of fatigue of muscles based on the muscular strength electromyograms and reported a method of measuring and comparing the areas of electromyograms ("Industrial Medicine," Vol. 20, No. 2, 1978, pp. 94 to 104). According to this method, the areas of electromyograms can be found by forming the envelopes thereof as shown in FIG. 9. However, this method has the disadvantage that not only is there a considerable error in drawing envelopes due to differences of individuals, but also it is a time consuming and troublesome work to obtain the envelopes.

To overcome these shortcomings it was necessary to find the ratio between the integrals of the muscular strength and the electromyogram to display it.

On the other hand, the muscular strength depends on the constitution or physique of the individual. The extent of the constitution can be represented by the body weight. Since a person of a lighter weight is lower in the muscular strength than a person of a heavier weight, the ratio between the integrated values of the electromyogrammatic amplitude to muscular strength is smaller even though the integrated values of the electromyogrammatic amplitudes are the same. This fact suggests that the numerical values of subjects of different weights cannot be compared as they are.

The present invention has overcome these difficulties.

DISCLOSURE OF THE INVENTION

The present invention is to derive the variation in the muscular strength such as dorsal muscular strength, shoulder arm strength, grasping power, or the like through a transducer as an electric signal and, at the same time, to record the electromyogrammatic waveform induced from the necessary part of the muscle to be tested, the variation in the muscular strength and the electromyogrammatic waveform being processed for digital representation of the maximum muscular strength and the maximum amplitude, respectively, and the ratio between the integrated values of the electromyogrammatic amplitude to the muscular strength being corrected by the weight/muscular strength coefficient for digital representation thereof.

The present invention employs a dorsal muscular strength, shoulder arm strength, or grasping power meter and applies electrodes to the right and left neck regions, an upper part of the trapezius muscle, the deltoid muscle, an interscapular region or space, a lumbodorsal region, the pectoralis major muscle, the antebrachial muscle, etc. to induce and measure the myoelectric signals.

Since electric signals obtained from these parts cannot be displayed digitally as they are, they are subjected to waveform processing and the signal components of 10 Hz or less and 150 Hz or more which do not appear on an electromyogrammatic meter are removed by means of a high-pass filter and a low-pass filter and then the electric signals are transformed by a full-wave rectifier circuit into waveforms so that they can be easily supplied to a digital processor. Then, envelope signals are formed from these waveforms and passed through a low-pass filter which passes 3 Hz or less to get rid of fine variations and finally supplied to a display.

On the other hand, separately therefrom, a signal derived from the muscular strength through a transducer and an amplifier is supplied to a processing indicator through a delay circuit to be processed after being delayed by the time equal to the delay time resulting from the waveform processing.

While a person of less fatigue has a high muscular strength and a low discharge amount, a person of more fatigue or pain has a lower muscular strength and a higher discharge amount. To know the degree of fatigue or pain it is necessary to find the ratio of the discharge amount to the muscular strength (AMS ratio). However, since the muscular strength depends on the constitution or physique, to make a comparison between subjects on the same basis it is necessary to effect a weight correction.

The increase in the muscular strength is not proportional to increases in weight, but its ratio (weight/muscular strength coefficient) is proportional to the weight raised to the power of $\frac{2}{3}$. Thus, the weight correction value is, when the reference weight is assumed to be 50 Kg, as follows:

$$P = 50 \times (W/50)^{\frac{2}{3}}$$

where
P=weight correction value
W=weight

The progressive tendency of this correction value is 50 for a weight of 50 Kg, 56.5 for 60 Kg, 62.8 for 70 Kg, 68.4 for 80 Kg, 74.0 for 90 Kg, 79.4 for 100 Kg, while 43.1 for 40 Kg, 35.6 for 30 Kg, and 27.1 for 20 Kg.

When the weight correction is made with these values, the discharge amount/muscular strength ratio is multiplied by P/50. The correction factor is ×1 for the weight of 50 Kg and ×79.4/50 (=1.59) for 100 Kg, for example. The above-mentioned reference weight is not necessarily 50 Kg. It can be replaced by any numerical value.

Since the AMS ratio obtained by this method has been affected by a weight correction, the fatigue and pain of subjects of different weights can be compared on the basis of the same criterion.

BRIEF DESCRIPTION OF THE DRAWINGS

FIG. 9 is a diagram showing the method of finding the areas of electromyogrammatic waveforms 3 and 4 in FIG. 5 by means of envelopes.

BEST MODE OF CARRYING OUT THE INVENTION

Figure 1:
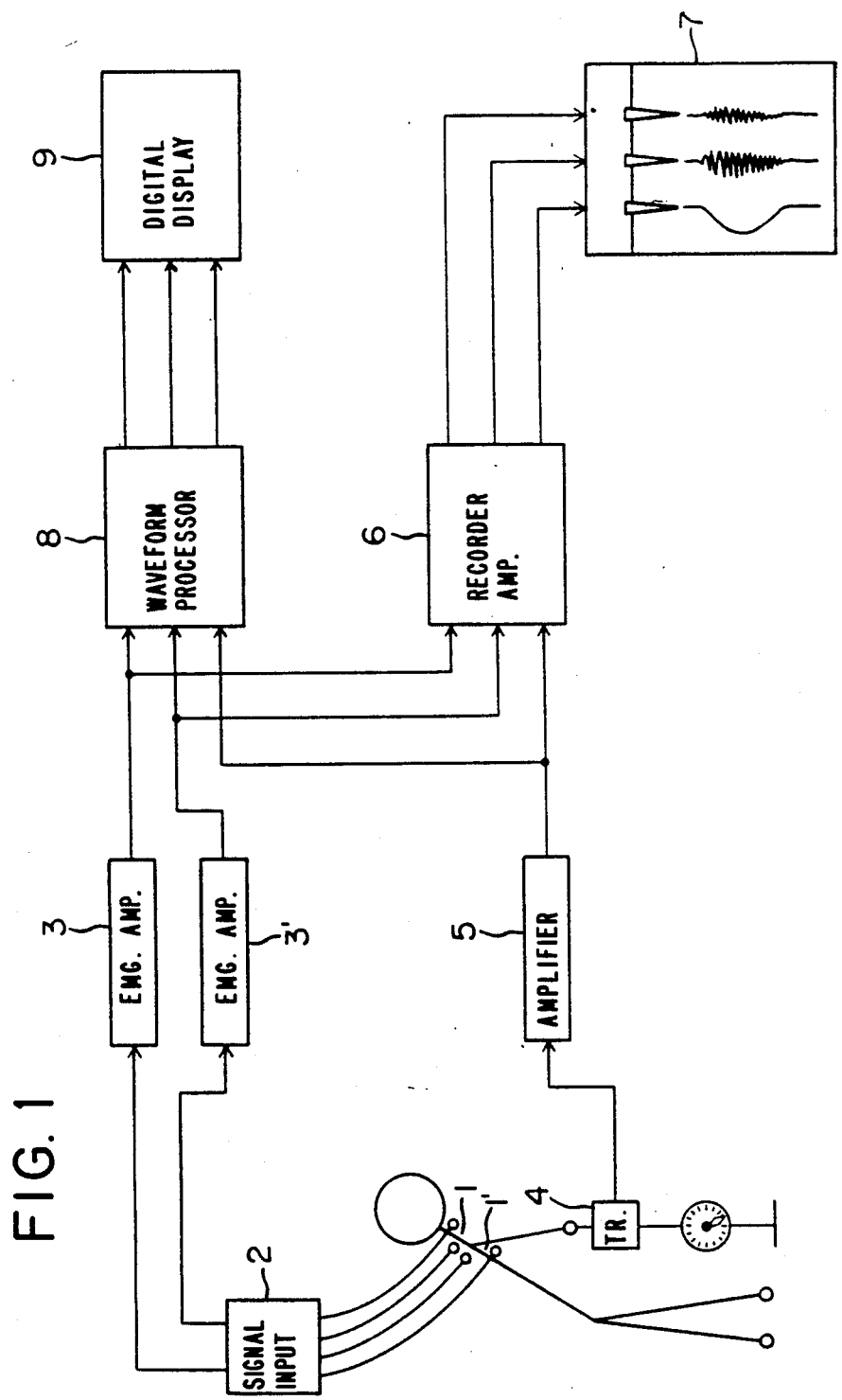
FIG. 1 is a block diagram of the apparatus of the present invention.

A preferred form of the present invention will be described with reference to the drawings, wherein FIG. 1 is a block diagram of a dorsal muscular strength meter for the measurement of muscular strength. An action potential is picked up from the muscle to be tested by surface electrodes 1 and 1' applied thereto and supplied through an input part 2 to electromyogram amplifiers 3 and 3' for amplification. The muscular strength of the muscle to be tested is separately transformed into an electric signal through a transducer 4 and then supplied to an amplifier 5. The muscular strength and electromyogram signals derived from the devices 3, 3' and 5 are recorded on a penrecorder 7 as a muscular strength diagram and electromyograms through a recorder amplifier 6. Separately therefrom, the electromyogram waveforms and the muscular strength derived from the devices 3, 3' and 5 are supplied to a waveform processor 8 to facilitate supplying the maximum values of the electromyogram waveforms and the muscular strength recorded on the penrecorder to a digitally processing display 9 and, at the same time, to facilitate the supply of the ratio between the integrated values of the electromyogrammatic amplitude to the muscular strength to the display 9.

Figure 2:
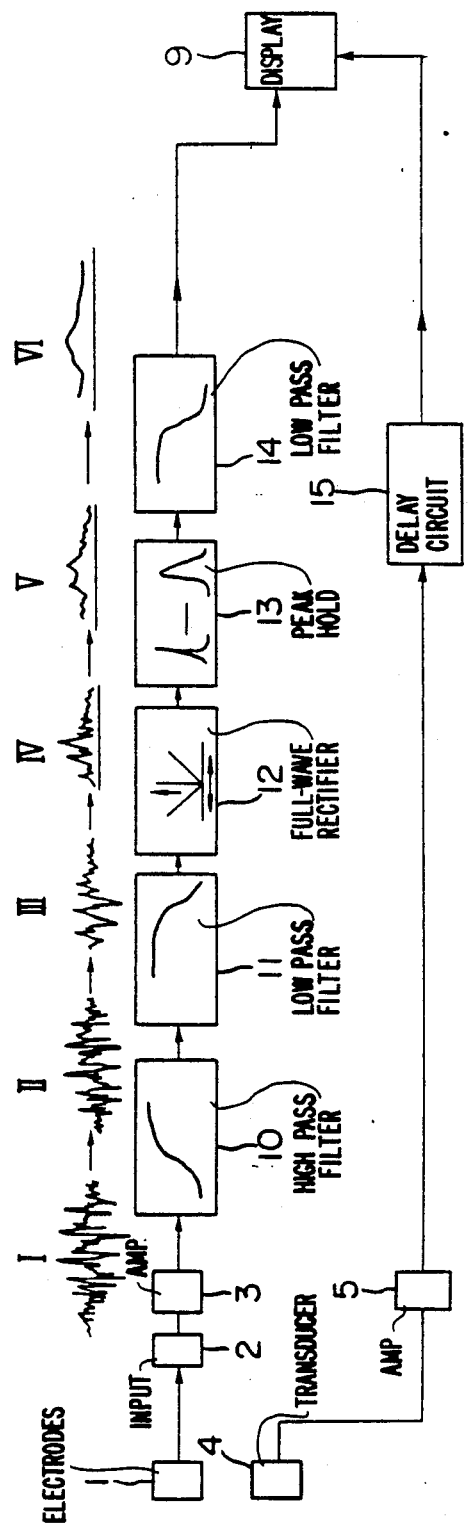
FIG. 2 is a block diagram of a waveform processor.

FIG. 2 is a block diagram associated with this waveform processor. The signal I produced by the devices 3 and 3' is shaped into the waveform II and III by removing therefrom a low signal component of 10 Hz or less due to the movement of the electrode and a signal component of 150 Hz or more which is not recorded on a penrecorder as an electromyogram by means of a high-pass filter (10) and a low-pass filter (11), respectively. The electromyogram waveform shaped into the waveforms II and III is transformed by a full-wave rectifier circuit 12 into the waveform IV which is facilitated to be supplied to a digitally processing display 9.

If the rectified electromyogrammatic waveform IV is directly supplied to the processing display 9, merely an average value of the signal is recorded which is of a different value from that visually observed on a penrecorder. Therefore, the rectified electromyogrammatic waveform IV is converted into an envelope signal V thereof through a peak hold circuit 13 which has a discharge time longer than the charging time. The signal V is further passed through a low-pass filter 14 which passes signals of 3 Hz or less to get rid of fine variations and then supplied to the processing display 9.

Separately therefrom, a muscular strength signal picked up through the transducer 4 and the amplifier 5 is delayed by a delay circuit 15 by the time equal to the time delay due to the wave processing and then supplied to the processing display 9.

Figure 3:
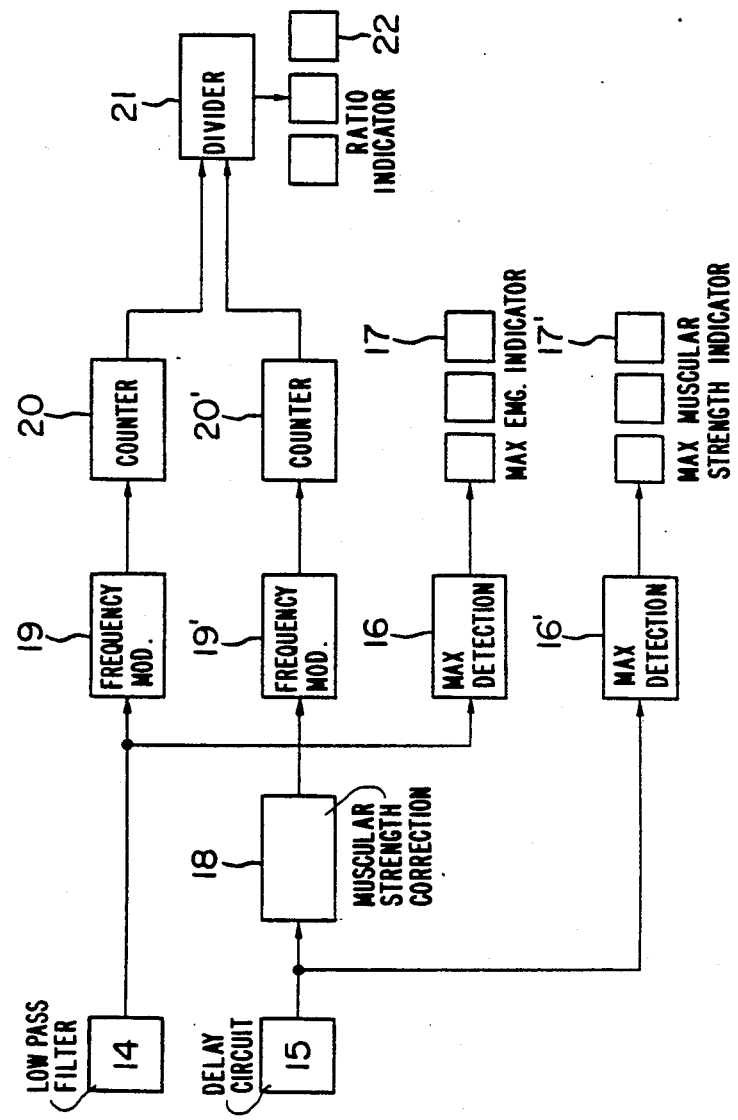
FIG. 3 is a block diagram of a digital processor.

FIG. 3 is a block diagram of the digitally processing display 9. A part of the signal which was waveform-processed by the low-pass filter 14 in FIG. 2 is counted by a counter circuit 20 after passing through a frequency modulator 19 and supplied to a divider 21. The rest of the signal from the low-pass filter 14 passes through a maximum detection circuit 16 and enters an electromyogram maximum value indicator 17 where the maximum amplitude is indicated by a numerical value of three digits.

A part of the muscular strength signal from the delay circuit 15 enters, after passing through the muscular strength correction circuit 18 and a frequency modulator 19', a counter 20' where it is counted and then enters the divider 21. The rest of the signal from the delay circuit 15 passes through a maximum value detection circuit 16' and then enters a muscular strength maximum value indicator 17' where the maximum muscular strength is indicated by a numerical value of three digits.

From the signals supplied from the counter circuit 20 and 20' a divider 21 processes the ratio between the integrated values provided by the low-pass filter 14 and the delay circuit 15. The processed ratio is indicated on an indicator 22 as a numerical value of three digits. Thus, in order to cause the start and the end of integration processing of the muscular strength and the electromyogram at the same time, an adjustment is made such that the integration starts when the muscular strength rises to a set level from the zero level and stops when the muscular strength returns to the same set level.

The numerical values indicated on the muscular strength maximum value indicator 17' and the electromyogram maximum value indicator 17 show under what functional conditions of the body the ratio between the integrated values indicated on the indicator 22 was obtained. For example, for the same ratio between the integrated values, the muscular strength and the electromyogram of a subject of inexhaustible vitality show high numerical values, whereas those of a subject of reduced vitality show low numerical values. Consequently, while the numerical value of the ratio between the integrated values alone cannot enable judgment of functional conditions of a subject, the indication of the maximum values of the muscular strength and the electromyogram enables the functional conditions of the body to be known.

Figure 4:
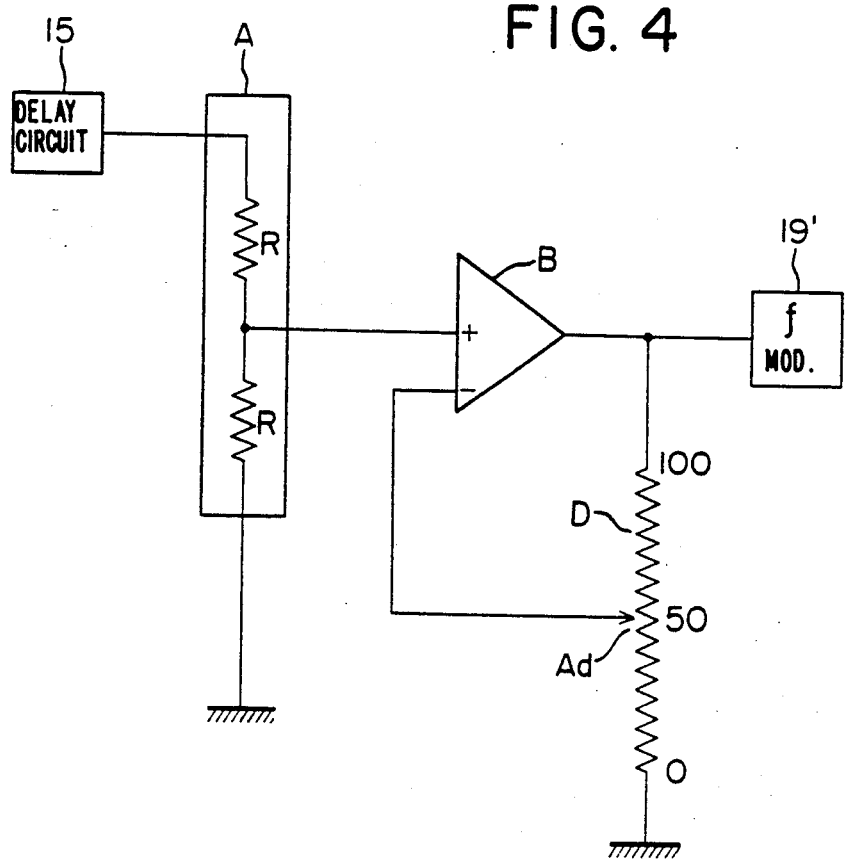
FIG. 4 is a weight correction circuit.

FIG. 4 shows a muscular strength correction circuit 18 for correcting the muscular strength with the body weight. A muscular strength signal derived from the delay circuit 15 is supplied to an attenuator A the output of which is supplied to an amplifier B. The adjusting point Ad of a divider D is set at a point higher or lower than 50 the by the adjustment value P of the weight adjuster on the panel of FIGS. 6 to 8. Thus, the signal supplied from the delay circuit 15 is amplified 50/P times and divided and indicated through the frequency modulator 19' and the counter circuit 20'. The correction value P can also be set automatically by inputting the weight of the subject.

Examples of experiments according to the present invention will be described with reference to FIGS. 5 to 8. The electrodes employed were dish-shaped surface electrodes which were applied to the parts to be tested at an interval of 50 mm. The calibration voltage was 40 mm/200 Kg for the dorsal muscular strength and 10 mm/1 mV for the electromyogram, and the time constant was 0.01 sec.

Figure 5:
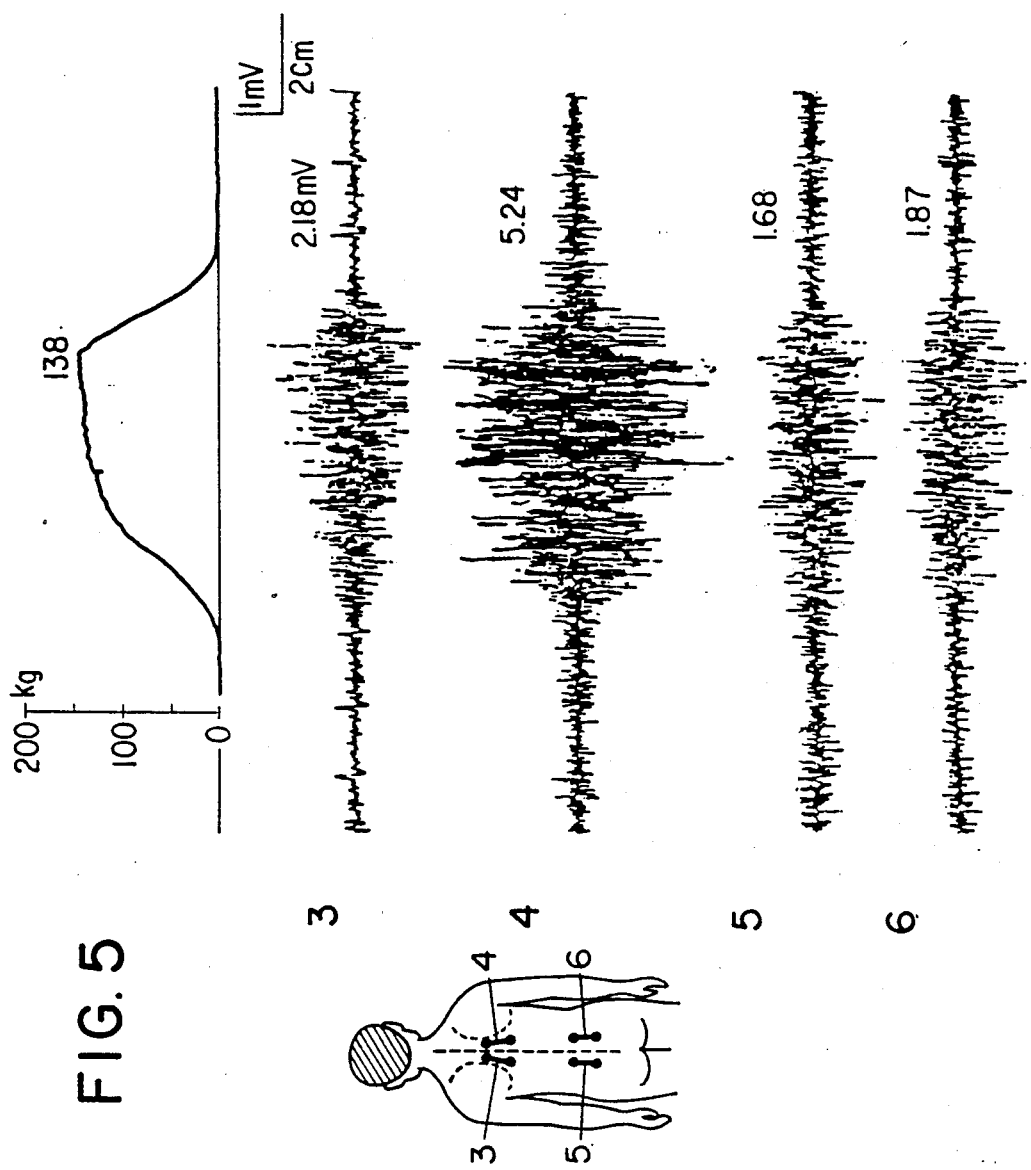
FIGS. 5 to 8 are embodiments of the present invention.

FIG. 5 is a record of the result of measurement of the dorsal muscular strength electromyogram of a 22-year-old male subject who feels oppressed at the right interscapular region. Electrodes were applied to the parts to be tested of the human body diagram on the left in FIG. 5 to measure the dorsal muscular strength and at the same time to record the electromyogram induced from the muscle to be tested. The dorsal muscular strength was recorded on channel 2, the myoelectric signals from right and left interscapular regions were recorded on channels 3 and 4, the myoelectric signals from right and left lumbodorsal muscles on channels 5 and 6, all these being, at the same time, supplied to a data recorder.

Studying FIG. 5 it can be seen that the maximum dorsal muscular strength is 138 Kg. This can be understood also from the muscular strength scale. An actual measurement of the maximum height of the curve shows 27.5 mm. Therefore, it is 138 Kg also considering the above calibration voltage. Next, in order to calculate the maximum values of the electromyogrammatic amplitudes, the space between the horizontal lines drawn above and below the amplitudes were measured. They were 2.18, 5.24, 1.68 and 1.87 mV for Channels 3, 4, 5 and 6, respectively, in view of the above calibration voltage. These maximum values are all indicated on the panels of FIGS. 6 to 8. That is, on the left display window of the panel there is digitally indicated the maximum dorsal muscular strength of 138 Kg, and 2.18, 5.24, 1.68 and 1.87 mV are digitally displayed on the upper display window Channels 3, 4, 5 and 6, respectively.

Figure 6:
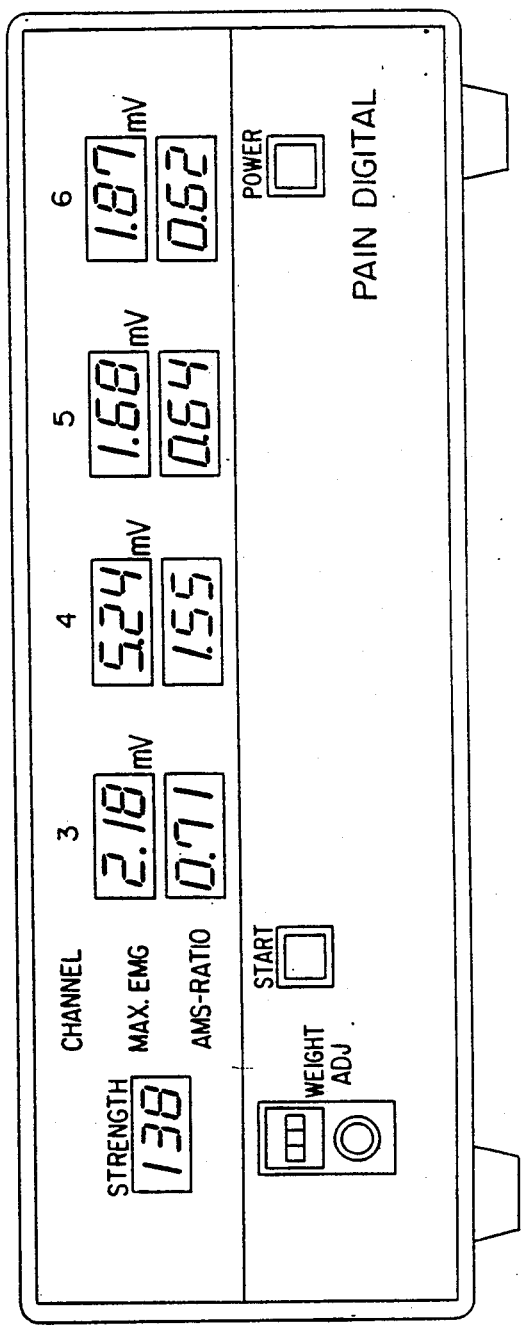
Figure 7:
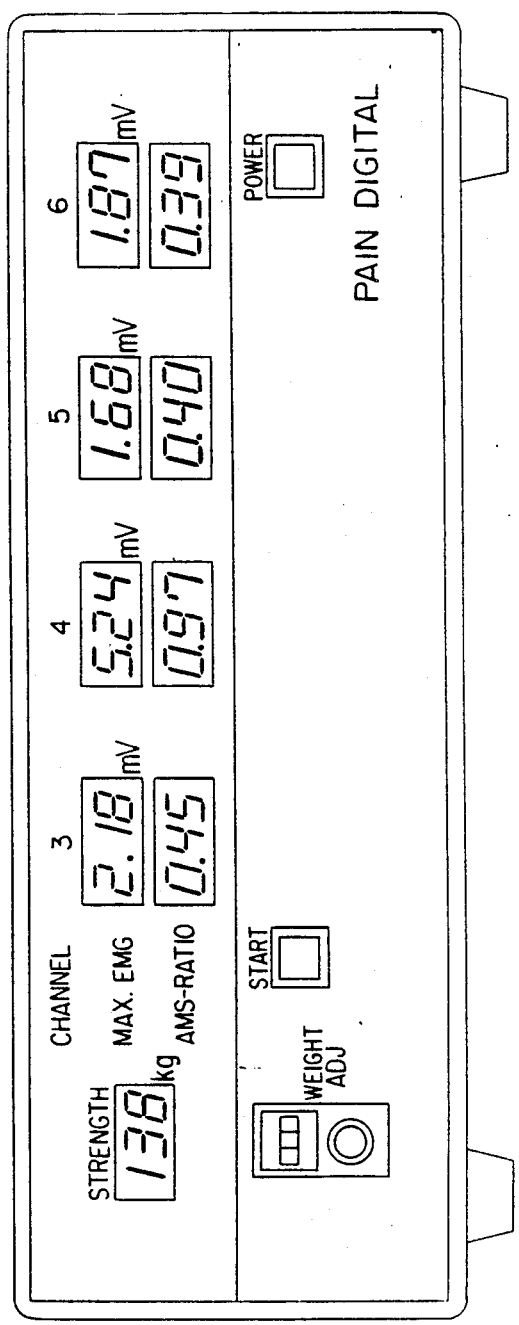
Figure 8:
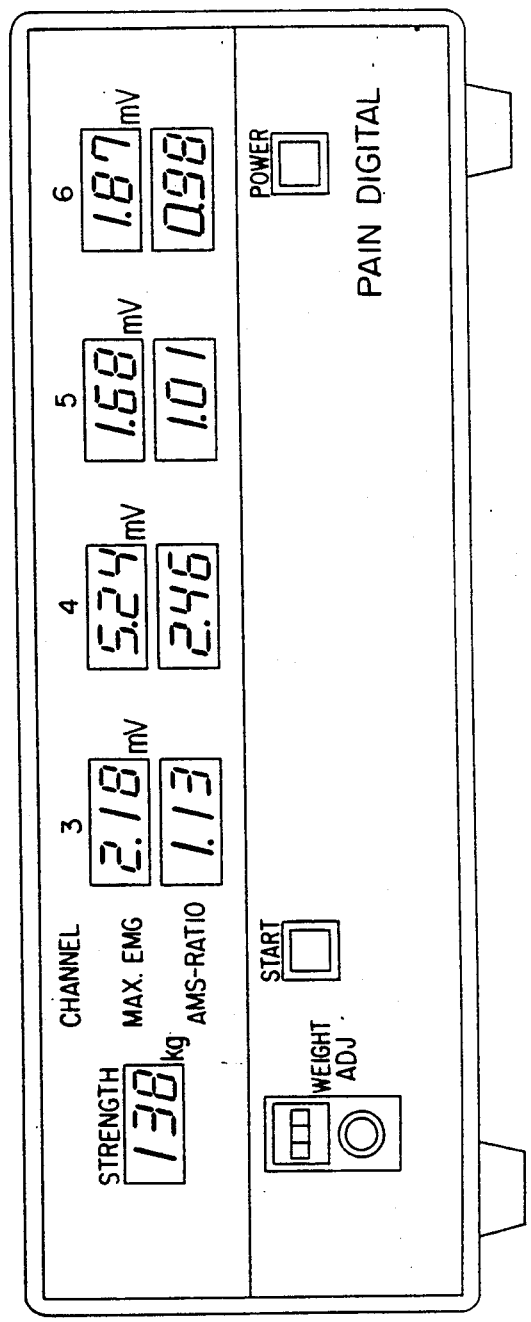

The ratios between the integrated values of the electromyogrammatic amplitude to the muscular strength corrected by the weight/muscular coefficient according to the present invention are displayed on the lower display windows of the panels of FIGS. 6 to 8. These are AMS ratios when the measurement records of FIG. 5 are retrieved and the correction value P is set for the weights of 50 Kg, 25 Kg and 100 Kg, respectively.

FIG. 6 is the case of the weight: 50 Kg. The correction value was set at 50.0. The lower display windows of the panel displayed 0.71, 1.55, 0.64 and 0.62 on the channels 3, 4, 5 and 6, respectively.

FIG. 7 is the case of the weight: 25 Kg. The correction value was set at 31.5. The lower display windows of the panel displayed 0.45, 0.97, 0.40 and 0.39 on the channels 3, 4, 5 and 6, respectively.

FIG. 8 is the case of the weight: 100 Kg. The correction value was set at 79.4. The lower display windows of the panel displayed 1.13, 2.46, 1.01 and 0.98 on the channels 3, 4, 5 and 6, respectively.

The following table is a comparison between the variation in the above displayed values and the increase in the weight.

| Weight Kg | Correction Value | Maximum Muscular Strength Kg | Channel | | | |
|---|---|---|---|---|---|---|
| | | | 3 | 4 | 5 | 6 |
| 25 | 31.5 | 138 | 0.45 | 0.97 | 0.40 | 0.39 |
| 50 | 50.0 | 138 | 0.71 | 1.55 | 0.64 | 0.62 |
| 100 | 79.4 | 138 | 1.13 | 2.46 | 1.01 | 0.98 |

While the maximum amplitudes at the upper parts of the display panels of FIGS. 6 to 8 the discharge amount 1.87 mV on the channel 6 is higher than 1.68 mV on the channel 5, in the lower windows the channel 5 indicates 1.01 and the channel 6 indicates 0.98. Thus, the indication of the channel 5 is higher than that of the channel 6. This is because the frequency of the electromyogrammatic amplitude was 70 Hz for the channel 5 in contrast to 50 Hz for the channel 6. For this reason the channel 5 displayed a higher value in the integration ratio.

As described above, the inventor has done research and development for a long time on the muscular strength electromyogram in order to measure the fatigue and pain of muscles. As shown in FIG. 5 the fatigue and pain of muscles are clearly numerically expressed. This numerical value is one supporting the appeal of the subject that he feels oppressed at the right interscapular region.

INDUSTRIAL FEASIBILITY

The present invention measures the fatigue and pain of muscles and expresses them numerically which no one could have done before. The results can be displayed exactly and in very short time as described above. The method of the present invention is characterized in that not only the results of the processing can be displayed exactly and in a very short time as described above, but also the ratio between the integrated values of the electromyogrammatic amplitude to the muscular strength is digitally displayed after being corrected by weight/muscular strength coefficient so that the displayed values can be compared under the same condition even if there is imbalance in the displayed values due to the difference in the weight.

I claim:

1. A method for detecting muscle fatigue comprising the steps of:
   (a) transforming the muscular strength of a muscle of a subject being examined into an electric muscular strength signal;
   (b) adjusting the muscular strength signal by a weight-muscular strength coefficient to provide an adjusted muscular strength signal;
   (c) detecting a myoelectric discharge from the muscle being examined to form an electromyogrammatic signal;
   (d) respectively integrating said electromyogrammatic signal and said adjusted muscular strength signal; and
   (e) determining the ratio between the integrated electromyogrammatic signal and the integrated adjusted muscular strength signal.

2. A method according to claim 1, wherein said weight-muscular strength coefficient is represented by the formula:

$$P = W_o \times (W/W_o)^{\frac{2}{3}}$$

wherein $W_o$ is a reference weight and W is the weight of said subject, and said muscular strength signal is adjusted by multiplication by $P/W_o$.

3. A method according to claim 1, wherein the step (e) comprises dividing said integrated electromyogrammatic signal by said integrated adjusted muscular strength signal to derive said ratio.

4. A method according to claim 1, further comprising the step of displaying said ratio.

5. A method according to claim 4, further comprising the step of displaying a maximum value of said electromyogrammatic signal.

6. A method according to claim 4, further comprising the step of displaying a maximum value of said muscular strength signal.

7. A method according to claim 5, further comprising the step of displaying a maximum value of said muscular strength signal.

8. A method according to claim 1, wherein the step (d) comprises respectively integrating a signal envelope of said electromyogrammatic signal and said adjusted muscular strength signal.

9. A method according to claim 1, wherein the step (d) comprises:
   (d1) detecting a signal envelope of said electromyogrammatic signal;
   (d2) frequency-modulating a carrier signal with the detected envelope so that the instantaneous frequency of the modulated carrier signal varies as a function of the instantaneous value of said envelope;
   (d3) counting the oscillations of said modulated carrier signal to provide a count value representative of the integrated electromyogrammatic signal;
   (d4) frequency-modulating a second carrier signal with the adjusted muscular strength signal so that the instantaneous frequency of the modulated second carrier signal varies as a function of the instantaneous value of said adjusted muscular strength signal; and
   (d5) counting the oscillations of said modulated second carrier signal to provide a count value representative of the integrated adjusted muscular strength signal.

10. A method according to claim 9, wherein the step (e) comprises determining the ratio between the count value of step (d3) and the count value of step (d5) as a digital value, and displaying said digital value by a display of decimal numbers.

11. An apparatus for detecting muscle fatigue comprising:
    (a) means including a transducer for transforming the muscular strength of a muscle of a subject being examined into an electric muscular strength signal;
    (b) means for adjusting the muscular strength signal by a weight-muscular strength coefficient to provide an adjusted muscular strength signal;
    (c) means for detecting a myoelectric discharge from the muscle being examined to form an electromyogrammatic signal;
    (d) means for integrating said adjusted muscular strength signal;
    (e) means for integrating said electromyogrammatic signal; and
    (f) means for determining the ratio between the integrated electromyogrammatic signal and the integrated adjusted muscular strength signal.

12. An appartus as claimed in claim 11, wherein said means for adjusting provides said adjusted muscular strength signal by multiplication of said muscular strength signal by $P/W_o$, where P is said weight-muscular strength coefficient and is represented by the formula:

$$P = W_o \times (W/W_o)^{\frac{2}{3}}$$

wherein $W_o$ is a reference weight and W is the weight of said subject.

13. An apparatus according to claim 11, wherein said ratio determining means comprises means for dividing said integrated electromyogrammatic signal by said integrated adjusted muscular strength signal.

14. An apparatus according to claim 11, further comprising means for displaying said ratio.

15. An apparatus according to claim 11, further comprising means for displaying a maximum value of said electromyogrammatic signal.

16. An apparatus according to claim 14, further comprising means for displaying a maximum value of said muscular strength signal.

17. An apparatus according to claim 11, wherein said means for integrating said electromyogrammatic signal includes means for detecting a signal envelope of said electromyogrammatic signal and means for integrating the detected envelope.

18. An apparatus according to claim 17, wherein said means for integrating said detected envelope comprises a first frequency modulator for modulating a carrier signal with the detected envelope so that the instantaneous frequency of the modulated carrier signal varies as a function of the instantaneous value of said envelope, and a first counter for counting the oscillations of said modulated carrier signal to provide a count value representative of the integrated electromyogrammatic signal; and
    wherein said means for integrating said adjusted muscular strength signal comprises a second frequency modulator for modulating a second carrier signal with the adjusted muscular strength signal so that the instantaneous frequency of the modulated second carrier signal varies as a function of the instantaneous value of said adjusted muscular strength signal; and a second counter for counting the oscillations of said modulated second carrier signal to provide a count value representative of the integrated adjusted muscular strength signal.

19. An apparatus according to claim 18, wherein said ratio determining means comprises means for determining the ratio between the count value of said first counter and the count value of said second counter as a digital value, and displaying said digital value by a display of decimal numbers.

20. An apparatus according to claim 18, wherein said means for detecting a myoelectric discharge comprises:
a pair of electrodes adapted to be placed on the muscle being examined to generate a raw electromyogrammatic (EMG) signal having alternating amplitudes;
filter means for filtering out components of said raw EMG signal having a frequency greater than a first value and less than a second value to produce a filtered EMG signal; and
rectifier means connected to said filter means for rectifying said filtered EMG signal, and
wherein said envelope detecting means is connected to said rectifier means.

21. A method for detecting muscle fatigue comprising the steps of:
(a) transforming the muscular strength of a muscle of a subject being examined into an electric muscular strength signal;
(b) detecting a myoelectric discharge from the muscle being examined to form an electromyogrammatic signal;
(c) respectively integrating said electromyogrammatic signal and said muscular strength signal; and
(d) determining the ratio between the integrated electromyogrammatic signal and the integrated muscular strength signal.

22. A method according to claim 21, wherein the step (c) comprises the steps of:
(c1) frequency-modulating a carrier signal with said electromyogrammatic signal so that the instantaneous frequency of the modulated carrier signal varies as a function of the instantaneous value of said electromyogrammatic signal;
(c2) counting the oscillations of said modulated carrier signal to provide a first count value representative of the integrated electromyogrammatic signal;
(c3) frequency-modulating a second carrier signal with said muscular strength signal so that the instantaneous frequency of the modulated second carrier signal varies as a function of the instantaneous value of said muscular strength signal; and
(c4) counting the oscillations of said modulated second carrier signal to provide a second count value representative of the integrated muscular strength signal;
wherein the step (d) comprises dividing said first count value by said second count value to derive said ratio.

23. A method according to claim 22, further comprising the step of displaying said ratio as a digital value by decimal numbers.

24. A method according to claim 23, further comprising the step of digitally displaying a maximum value of said electromyogrammatic signal by decimal numbers.

25. A method according to claim 23, further comprising the step of digitally displaying a maximum value of said muscular strength signal by decimal numbers.

26. A method according to claim 24, further comprising the step of digitally displaying a maximum value of said muscular strength signal by decimal numbers.

27. An apparatus for detecting muscle fatigue comprising:
(a) means for transforming the muscular strength of a muscle of a subject being examined into an electric muscular strength signal;
(b) means for detecting a myoelectric discharge from the muscle being examined to form an electromyogrammatic signal;
(c) first integrator means for integrating said electromyogrammatic signal;
(d) second integrator means for integrating said muscular strength signal; and
(e) means for determining the ratio between the integrated electromyogrammatic signal and the integrated muscular strength signal.

28. An apparatus according to claim 27, wherein said first integrator means comprises a first frequency modulator for modulating the frequency of a carrier signal with said electromyogrammatic signal so that the instantaneous frequency of the modulated carrier signal varies as a function of the instantaneous value of said electromyogrammatic signal, and a first counter for counting the oscillations of said modulated carrier signal to provide a first count value representative of the integrated electromyogrammatic signal;
wherein said second integrator means comprises a second frequency modulator for modulating the frequency of a second carrier signal with said muscular strength signal so that the instantaneous frequency of the modulated second carrier signal varies as a function of the instantaneous value of said muscular strength signal, and a second counter for counting the oscillations of said modulated second carrier signal to provide a second count value representative of the integrated muscular strength signal; and
wherein said ratio determining means includes means for dividing said first count value by said second count value to derive said ratio.

29. An apparatus according to claim 28, further comprising means for displaying said ratio as a digital value in decimal numbers.

30. An apparatus according to claim 29, further comprising:
means for detecting a maximum amplitude of said electromyogrammatic signal and representing the detected maximum amplitude as a digital value; and
means for displaying said digital value by decimal numbers.

31. An apparatus according to claim 29, further comprising:
means for detecting a maximum amplitude of said muscular strength signal and representing the detected maximum amplitude as a digital value; and
means for displaying said digital value by decimal numbers.

* * * * *

UNITED STATES PATENT AND TRADEMARK OFFICE
CERTIFICATE OF CORRECTION

PATENT NO. :   4,667,513
DATED      :   May 26, 1987
INVENTOR(S):   Yoshio Konno, Tokyo, Japan It is certified that error appears in the above-identified patent and that said Letters Patent is hereby corrected as shown below:

ON THE TITLE PAGE:

The first name of the Inventor should be spelled Yoshio, not Yohio.

Signed and Sealed this

Eighth Day of November, 1988

Attest:

DONALD J. QUIGG

*Attesting Officer*            *Commissioner of Patents and Trademarks*